US012759957B2

(12) United States Patent
Schmidt

(10) Patent No.: US 12,759,957 B2
(45) Date of Patent: Oct. 13, 2026

(54) CATALYSTS, PREPARATION METHOD THEREOF, AND SELECTIVE HYDROGENATION PROCESSES

(71) Applicant: W. R. Grace & Co.—Conn., Columbia, MD (US)

(72) Inventor: Stephen R. Schmidt, Silver Spring, MD (US)

(73) Assignee: W.R. Grace & Co.—Conn, Columbia, MD (US)

( * ) Notice: Subject to any disclaimer, the term of this patent is extended or adjusted under 35 U.S.C. 154(b) by 919 days.

(21) Appl. No.: 17/915,995

(22) PCT Filed: Mar. 24, 2021

(86) PCT No.: PCT/US2021/023843
§ 371 (c)(1),
(2) Date: Sep. 29, 2022

(87) PCT Pub. No.: WO2021/202188
PCT Pub. Date: Oct. 7, 2021

(65) Prior Publication Data

US 2023/0147998 A1 May 11, 2023

Related U.S. Application Data

(60) Provisional application No. 63/001,652, filed on Mar. 30, 2020.

(51) Int. Cl.

| | |
|---|---|
| ***C07C 29/17*** | (2006.01) |
| ***B01J 8/02*** | (2006.01) |
| ***B01J 23/755*** | (2006.01) |
| ***B01J 37/06*** | (2006.01) |

(52) U.S. Cl.
CPC ............... *C07C 29/172* (2013.01); *B01J 8/02* (2013.01); *B01J 23/755* (2013.01); *B01J 37/06* (2013.01); *C07C 2521/04* (2013.01); *C07C 2523/72* (2013.01); *C07C 2523/755* (2013.01)

(58) Field of Classification Search
CPC ... B01J 8/02; B01J 23/755; B01J 37/06; B01J 25/02; C07C 29/172; C07C 2521/04; C07C 2523/72; C07C 2523/755
See application file for complete search history.

(56) References Cited

U.S. PATENT DOCUMENTS

| | | | | |
|---|---|---|---|---|
| 2,953,605 | A | 9/1960 | Hort et al. | |
| 3,950,441 | A * | 4/1976 | Rudoff | B01J 23/8892 568/861 |
| 6,277,895 | B1 | 8/2001 | Zhou et al. | |
| 2008/0221371 | A1 | 9/2008 | Lorenz et al. | |
| 2010/0016643 | A1 | 1/2010 | Pinkos et al. | |
| 2016/0333452 | A1* | 11/2016 | Johnson | C30B 29/52 |

FOREIGN PATENT DOCUMENTS

| | | | |
|---|---|---|---|
| CN | 106824199 | A | 6/2017 |
| CN | 106861701 | A | 6/2017 |
| CN | 109647409 | A | 4/2019 |
| WO | WO-2012/095777 | A1 | 7/2012 |
| WO | WO-2020/033358 | A1 | 2/2020 |

OTHER PUBLICATIONS

International Search Report and Written Opinion issued in International Patent Application No. PCT/US2021/23843, dated Aug. 13, 2021.
Palacio et al., "Total oxidation of toluene over calcined trimetallic hydrotalcites type catalysts" 2010 Journal of Hazardous Materials vol. 177, pp. 407-403.
Wikipedia "Copper" Dec. 16, 2019. Retrieved from https://en.wikipedia.org/w/index.php?title=Copper&oldid=931036689.
Wikipedia "Raney nickel" Nov. 4, 2019. Retrieved from https://en.wikipedia.org/w/index.php?title=Raney_nickel&oldid=924623796.
JP Office action for application 2022-559534 Mailed Oct. 22, 2024, 7 pages.
Tarama, Kimio, et al., Study on Kinetics of the Promoting Effect of Alkali on Raney Nickel, Journal of the Industrial Chemistry of Japan, 1958, vol. 61, No. 7, pp. 843-846, DOI: 10.1246/nikkashi1898.61.843 (document indicating a well-known art).
Foreign Search Report on EP 21780064 dated Feb. 14, 2024 (7 pages).
IPRP on PCT PCT/US2021/023843 dated Oct. 13, 2022 (10 pages).

* cited by examiner

*Primary Examiner* — Jafar F Parsa
(74) *Attorney, Agent, or Firm* — Dority & Manning, P.A.

(57) ABSTRACT

The present invention relates to a process for making 1,4-butanediol. The process may include reacting a solution comprising 1,4-butynediol with hydrogen in a presence of an effective amount of a catalyst. The catalyst may include copper.

4 Claims, No Drawings

CATALYSTS, PREPARATION METHOD THEREOF, AND SELECTIVE HYDROGENATION PROCESSES

The present application is the U.S. National Stage of International Patent Application No. PCT/US2021/023843, filed Mar. 24, 2021, which claims priority from U.S. Patent Application No. 63/001,652, filed Mar. 30, 2020, all of which are incorporated herein by reference in their entirety.

FIELD OF THE INVENTION

The present invention relates to catalysts, and more particularly, to catalysts for preparing 1,4 butanediol, a preparation method thereof, a selective hydrogenation process employing the catalysts, and an alloy precursor for preparing the catalysts.

BACKGROUND

Skeletal metal nickel catalyst in granular fixed bed form is generally used industrially to make butanediol (BDO), a component in making polyesters, from the unsaturated compound 1, 4 butynediol (BYD). One form of skeletal metal nickel catalyst is made by the Raney process, starting from alloys which contain at least two metals such as nickel and aluminum. Optionally, other metals or compounds are added in smaller amounts as 'promoters' to enhance activity, selectivity, or durability of the catalyst.

U.S. Pat. No. 6,262,317 discloses a process for preparing 1,4-butanediol by continuous catalytic hydrogenation of 1,4-butynediol. The process comprises reacting 1,4-butynediol with hydrogen in the liquid continuous phase in the presence of a heterogeneous hydrogenation catalyst. The catalyst generally comprises one or more elements of transition groups I, VI, VII and VIII of the Periodic Table of the Elements. The catalyst preferably further comprises at least one element selected from the elements of main groups II, III, IV and VI, transition groups II, III, IV and V of the Periodic Table of the Elements, and the lanthanides as a promoter to increase the activity. The promoter content of the catalyst is generally up to 5% by weight. The catalysts may be precipitation, supported, or skeletal type catalysts.

CN 201210212109.2 discloses a preparation and an activation method of a skeletal metal nickel-aluminum-X catalyst specially for hydrogenation preparation of 1,4-butanediol from 1,4-butynediol. X represents Mg, B, Sr, Cr, S, Ti, La, Sn, W, Mo or Fe.

U.S. patent application No. 62/715,926 discloses a process for making 1,4-butanediol. The process includes reacting a solution comprising 1,4-butynediol with hydrogen in a presence of a catalyst including cerium as a promotor. The process may reduce significantly formation of butanol byproduct.

The current catalysts typically have a predictable limited lifetime. The current process produces n-butanol, acetals (e.g. 2-(4-hydroxybutoxy) tetrahydrofuran), and other byproducts at a gradually increasing rate until a maximum specification limit is reached, which defines the end of useful life of the bed's catalyst. The acidic Al species present in a skeletal metal catalyst such as hydrous alumina residues from a leaching process are considered as one main cause in producing the byproducts including butanol and acetal. Skeletal metal catalysts may in general contain small amounts of added elements as promoters, whose functions include improvement of activity, selectivity and stability of the catalyst in the chemical environment of a given hydrogenation process. Some promoters for skeletal metals such as the conventional Mo, Cr, or Fe may actually increase formation of butanol byproduct due to the increasing surface acidity. Operating conditions such as relatively low temperature, relatively high pressure, and control of feed pH have been optimized previously and their combination still fails to suppress formation of butanol and acetal adequately. Butanediol is a main component in making polyesters. Because downstream usages have impurity limits on the butanediol, reducing contaminants in the butanediol during the process for making the butanediol can significantly reduce cost, for example, associated with separation (e.g. distillation) of the impurity from the butanediol later.

BRIEF SUMMARY

The present invention provides a process for making 1,4-butanediol from a 1,4-butynediol solution in a present of a catalyst, which includes copper. The process reduces significantly and unexpectedly the amount of a main byproduct, acetal (2-(4-hydroxybutoxy) tetrahydrofuran), in addition to maintaining desirable low levels of another key byproduct, n-butanol, in the final 1,4-butanediol product.

Accordingly, one example of the present invention is a process for making 1,4-butanediol. The process may include reacting a solution comprising 1,4-butynediol with hydrogen in a presence of a catalyst, which includes copper as a promoter.

Another example of the present invention is an alloy precursor for a catalyst for making 1,4-butanediol. The alloy precursor may include a first metal, a second metal, and copper in a range of about 1% to about 10% by weight of the alloy precursor.

Another example of the present invention is a catalyst for making 1,4-butanediol. The catalyst may be a skeletal metal catalyst, which includes copper as a promoter.

Another example of the present invention is a process of preparing a catalyst. The process may include melting and mixing copper, a first element, and a second element to form an alloy precursor, followed by activation using an alkali solution to form the catalyst. The first element may be Ni and the second element may be aluminum.

DETAILED DESCRIPTION

The present invention is described with reference to embodiments of the invention in order to provide a better understanding by those skilled in the art of the technical solutions of the present disclosure.

A number modified by "about" herein means that the number can vary by 10% thereof. A numerical range modified by "about" herein means that the upper and lower limits of the numerical range can vary by 10% thereof. Butanol, n-butanol and 1-butanol are all synonyms for our purposes and interchangeable.

One example of the present invention is a process for making 1,4-butanediol. The process may include reacting a solution which includes 1,4-butynediol with hydrogen in a presence of an effective amount of a catalyst, which includes copper as a promoter. "An effective amount of a catalyst" herein refers to the process achieving an overall conversion of at least about 95%, preferably at least about 99% of starting butynediol, with good selectivity to 1,4-butanediol. The promoter is a minor component in the catalyst comparing to other main components such as nickel and aluminum to enhance activity, selectivity, or durability of the catalyst.

The solution which includes 1,4-butynediol may be a technical-grade 1,4-butynediol which is in a form of an aqueous solution and can additionally contain, as insoluble or dissolved constituents, components from the butynediol synthesis, e.g. bismuth, aluminum or silicon compounds. The main solvent for the solution which includes 1,4-butynediol is usually water. The solution which includes 1,4-butynediol may also comprise other solvents such as methanol, ethanol, propanol, butanol or recycled 1,4-butanediol product. The solutions containing recycled 1,4 butanediol product may contain lower 1,4 butynediol content than those containing only water as a solvent. The 1,4-butynediol content in the solution is generally from 5 to 90% by weight, preferably from 10 to 80% by weight, particularly preferably from 10 to 50% by weight of the solution. In one embodiment, the solution which includes 1,4-butynediol is 100% pure butynediol.

The solution which includes 1,4-butynediol may have a pH in a range from about 4.0 to about 11.0, preferably about 7.5 to about 10.0. The solution pH may be inherent to the process conditions of butynediol quality, temperature, pressure, etc., or optionally achieved by adjustment with small amounts of dilute base such as NaOH solution.

The hydrogen required for the reaction is preferably used in pure form. But it can also contain further components such as methane and carbon monoxide. The hydrogen pressure applied to a fixed bed reactor for this process may be in a range from about 15 to about 30 MPa. The inlet temperature of the fixed bed reactor may be in a range from about 80° C. to about 120° C. The flow rate of the feed solution may be chosen by those skilled in the art, in combination with an effective amount of catalyst, to allow for a chosen rate of conversion, thereby achieving a desired overall level of conversion of the butynediol, i.e. reaction with hydrogen to form products. The chosen rate of conversion of the butynediol in turn depends on whether the process stream is partly recycled to the reactor inlet. For non-recycled process streams, the chosen conversion rate yields high overall % conversion, e.g. over 98 wt. % of 1,4 butynediol, in a 'single pass'. A similarly high level of overall conversion may also be achieved at variable rates, e.g. using partly recycled process streams in which 10-20% of the process stream at the reactor outlet is removed as final product, and the other 80-90% is returned to the inlet.

According to the present invention, the catalysts used are those which are capable of hydrogenating CC triple and double bonds to single bonds. The catalyst may be in a form of a fixed-bed, a slurry or suspension, or a combination thereof. In one embodiment, the catalyst is in the form of the fixed-bed, and may have a particle size in a range of about 1 mm to about 8 mm, preferably about 2 mm to about 5 mm. In another embodiment, the catalyst is in the form of the slurry or suspension, and may have a median particle size in a range of about 10 μm to about 100 μm, preferably about 20 μm to about 80 μm.

The catalyst may further include at least a first element selected from the group consisting of Ni, Co, Fe, and mixtures thereof In one embodiment, the first element is Ni. The catalyst may further include at least a second element selected from the group consisting of aluminum, molybdenum, chromium, iron, tin, zirconium, zinc, titanium, vanadium, and mixtures thereof. In one embodiment, the second element is aluminum.

The catalyst may be a skeletal metal catalyst. Suitable skeletal metal catalysts include skeletal metal nickel, skeletal metal cobalt, skeletal metal nickel/molybdenum, skeletal metal nickel/chromium, skeletal metal nickel/chromium/iron or rhenium sponge.

Copper may be present in the catalyst in an amount ranging from about 1.0% to 20.0%, preferably about 1.0% to about 12.0%, and more preferably about 2.0% to about 8.0% by weight of the catalyst.

The molar ratio of hydrogen to butynediol in the reactor may be at least 3:1, preferably from 4:1 to 100:1.

When a fixed-bed reactor is used in the process of the present invention, the space velocities of the solution and gas flowing through the fixed-bed of the catalyst are not limited. One of ordinary skill in the art can adjust the space velocities of the solution and gas to obtain optimum yield of 1,4-butanediol with a low amount of by products such as butanol and acetal.

The catalyst according to the present invention may comprise only one type of the catalyst or a mixture of several types of catalysts. The mixture of several types of catalysts can be present as pseudohomogeneous mixture or as a structured bed in which individual reaction zones each are composed of a pseudohomogenous catalyst bed. It is also possible to combine the methods, for example, to use one catalyst type at the beginning of the reaction and to use a mixture further downstream.

The process may produce acetal as a byproduct in a range of less than about 1.0% by weight, preferably less than about 0.5% by weight, more preferably less than about 0.25% by weight, based on a total weight of the acetal, butanol, and the 1,4-butanediol as the solution comprising 1,4-butynediol has a pH of 7.5 or higher.

In one embodiment of the process for making 1,4-butanediol, the catalyst is a skeletal element catalyst. The catalyst includes at least a first element selected from the group consisting of Ni, Co, Fe, and mixtures thereof, at least a second element selected from the group consisting of aluminum, molybdenum, chromium, iron, tin, zirconium, zinc, titanium, vanadium, and mixtures thereof, and copper as a promoter. The copper is present in an amount ranging from about 1.0% to about 12.0% by weight of the catalyst. The solution comprising 1,4-butynediol has a pH of about 4.0 to about 11.0. The process produces acetal as a byproduct in a range of less than about 1.0% by weight, preferably less than about 0.5% by weight, more preferably less than about 0.25% by weight, based on a total weight of the acetal, butanol, and the 1,4-butanediol as the solution comprising 1,4-butynediol has a pH of 7.5 or higher.

Another example of the present invention is an alloy precursor for a catalyst for making 1,4-butanediol. The alloy precursor may include a first metal, a second metal, and copper in a range of about 1.0% to about 10.0%, preferably about 2.0% to 7.0%, by weight of the alloy precursor.

In one embodiment, copper is in a range of about 2.0% to about 5.0% by weight of the alloy precursor.

In one embodiment, the first metal is Ni in a range of about 30% to about 60% by weight of the alloy precursor, and the second metal is Al in a range of about 40% to about 65% by weight of the alloy precursor. In another embodiment, the first metal is Ni in a range of about 40% to about 49% by weight of the alloy precursor, and the second metal is Al in a range of about 50% to about 60% by weight of the alloy precursor.

Another example of the present invention is a catalyst for making 1,4-butanediol. The catalyst may include a skeletal metal catalyst, which includes copper as a promoter. Copper may be present in the catalyst in an amount ranging from about 1.0% to about 10.0% by weight, preferably about 2.0% to about 8.0% by weight of the catalyst. In one embodiment comprising about 1.0% to about 10.0% by weight of copper, the first element of the skeletal metal is nickel and the second element of the skeletal metal is aluminum.

Another example of the present invention is a process of preparing a catalyst. The process may include melting and mixing copper, a first element, and a second element to form an alloy precursor.

The first element may be selected from the group consisting of Ni, Co, Fe, and mixtures thereof. The second element may be selected from the group consisting of aluminum, molybdenum, chromium, iron, tin, zirconium, zinc, titanium, vanadium, and mixtures thereof. In one embodiment, the first element is Ni and the second element is aluminum. Ni may be present in an amount ranging from about 30% to about 60% by weight, preferably about 40% to about 49% by weight, based on a total weight of the alloy precursor. Aluminum may be present in an amount ranging from about 40% to about 65% by weight, preferably from about 50% to 60% by weight, based on a total weight of the alloy precursor. Copper may be present in an amount ranging from about 1.0% to about 10.0% by weight, preferably from about 2.0% to about 6.0% by weight, based on a total weight of the alloy precursor.

In one embodiment, the process of preparing the catalyst further includes activating the alloy precursor by contacting it with an alkali solution. The alkali solution may be an aqueous solution of sodium hydroxide or potassium hydroxide having a concentration in a range of 1% to 25% by weight. In one embodiment, the alkali solution is pumped continuously through the alloy precursor bed to activate the alloy precursor. In another embodiment, the alloy precursor particles are added into the alkali solution in batches to activate the alloy precursor. In one embodiment, the catalyst is a skeletal metal catalyst.

In one embodiment, the process of preparing a catalyst includes melting and mixing copper, a first element, and a second element to form an alloy precursor and contacting the alloy precursor with an alkali aqueous solution to produce the catalyst. The first element is selected from the group consisting of Ni, Co, Fe, and mixtures thereof, and the second element is selected from the group consisting of aluminum, molybdenum, chromium, iron, tin, zirconium, zinc, titanium, vanadium, and mixtures thereof. Copper is present in an amount ranging from about 1.0% to about 10.0% by weight based on a total weight of the catalyst. In one embodiment comprising about 1.0% to about 12.0% by weight of copper, the first element of the skeletal metal is nickel and the second element of the skeletal metal is aluminum.

Another example of the present invention is the catalyst produced by the process of preparing the catalyst according to one embodiment of the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Hereinafter, the present invention will be described in more detail with reference to Examples. However, the scope of the present invention is not limited to the following Examples.

EXAMPLES

Example 1

Catalyst Preparation

An alloy precursor containing 58% by weight of Al, 2.5% by weight of Cu, and 39.5% by weight of Ni was formed by melting and mixing the three components. The alloy precursor was then crushed and sieved into alloy precursor particles in a range of 8-12 mesh size or having diameters in a range of about 2 mm to about 3 mm.

A 390 g portion of the alloy precursor particles was placed in a beaker to form a "bed." This bed of alloy precursor particles was converted to a portion of catalyst by contacting with a 'leachant,' which includes pumping five portions of aqueous NaOH solutions continuously through the alloy precursor bed at a constant rate. Each portion of the aqueous NaOH solutions is 18 liters, and the strength of the five portions was increasing during the process from 1%, then 2%, 3%, 4% to finally 5% respectively. Each portion of aqueous NaOH solution was delivered through the alloy precursor bed in 40 minutes while an immersed cooling coil (with internal water flow) is used to control the temperature of the process at a target of 38° C.

The catalyst was then washed with 2 liters of a 0.25% NaOH solution for 10 minutes, then with water at 45° C. until the effluent washing water reached a pH of 9.

This portion of catalyst had the following assay (wt. %) by ICP analysis: 54.6 Ni, 41.7 Al, 3.5 Cu, 0.2 Fe Catalytic testing The prepared catalyst was maintained in water-wetted state as it was loaded into a vertical column reactor with bed dimensions having an inner diameter of about 0.5 inches and a height of about 6 inches. This amounts to a catalyst bed having a volume of 18 mL.

Reactant feed solution was prepared by dissolving 1,4 butanediol at 40% (representing recycled 'BDO' product) along with 10% of 2-butyne-1,4 diol by weight in water. The overall organic compound content is nominally 50%, with water at 50%. The pH of this mixture when freshly made varied from about 4 to about 5.5. As a further variable for subsequent catalyst testing, additional portions of the reactant feed solution were prepared and then adjusted to pH in a range from about 7.0 to about 8.5, by addition of small amounts of 15% NaOH solution.

In catalyst testing, reaction conditions employed were: inlet temperature of 100° C., peak temperature: 150° C. (outlet temperature), hydrogen pressure=about 2500 psig (16-17 MPa), and a controllable liquid feed flow rate. 0.25 mL/min. is the default liquid flow rate; a range of 0.10-2.5 is feasible. When the flow rate is changed, it is then maintained at a constant level for several days to achieve steady levels of products. Co-current upward flow of $H_2$ gas (300 mL/min) and the liquid is maintained throughout the testing process.

Product assays, stated in wt. % of organic products, were determined by GC analysis, using a Restek Stabilwax 30×0.32×0.5 column, ethanol solvent at 90%, diglyme as internal standard, and flame ionization detector. Reported yields for each condition in Tables 1 and 2 are averages from samples taken after each 8 hours of continuous operation.

The main byproduct of interest, n-butanol ("BuOH") ranges from 0.23-0.35% over the various pH conditions. The butanol yield is lower when using a higher pH of the feed solution. A second by-product, 2-(4-hydroxybutoxy) tetrahydrofuran, the cyclized acetal formed by reaction of product and feed molecules and dehydration, is listed as 'acetal' in Tables 1 and 2. As shown in Table 1, acetal varies from 0.17 to 0.38% with different pHs.

The pH of the reactant feed solution employed, elapsed time at the pH condition, and summary of two key byproducts are listed in Table 1.

Example 2

Catalyst Preparation

Methods similar to those of example 1 were used, with the exception of the alloy being of composition: 58% by weight of Al, 3.8% by weight of Cu, and 38.2% by weight of Ni. The resulting catalyst composition was 42.6%Al, 52.3%Ni, 5.0% Cu, 0.2% Fe.

Catalyst Testing

Testing proceeds similarly to that of Example 1 to be conducted to show improvement over Ce—Ni and varying with Cu content as compared to Example 1.

Comparative Example (Ce—Ni)

Catalyst Preparation

The alloy precursor employed had the following composition: 61.5% Al, 34.9% Ni, 2.1% Ce. The activation and washing procedures were similar to that of Example 1 except that the concentrations of the NaOH solutions were 0.9, 1.75, 2.6, 3.5 and 4.35%, respectively. The resulting catalyst composition was 51.5% Al, 45.2% Ni, 3.3% Ce.

Catalyst Testing

Testing conditions and methods are as stated in Example 1. The testing results are shown in Table 2. As summarized in Table 2, butanol byproducts ranged from 0.21-0.55% and acetal ranged from 0.40-0.65 are obtained.

As shown in Tables 1 and 2, employing the catalyst according to one embodiment of the present invention shows significant improvement in lowering the amount of acetal byproduct by the use of copper rather than cerium as a promoter, while maintaining similar or slightly lower levels of butanol byproduct. These byproducts have maximum allowable values in full-scale industrial use. Thus, these reductions in acetal byproduct are very significant in industrial applications, thereby extending lifetime of fixed bed catalyst systems, often by increments of several months, translating to lower operating costs for the user. There are also other benefits such as lower cost and simpler usage with Cu metal comparing to $CeO_2$.

TABLE 1

BYD->BDO byproducts, Copper-Nickel

| feed pH | BuOH(%) | acetal(%) |
|---|---|---|
| 4.3 | 0.35 | 0.35 |
| 7.0 | 0.28 | 0.38 |
| 7.5 | 0.23 | 0.12 |
| 8.0 | 0.25 | 0.24 |
| 8.5 | 0.23 | 0.17 |

TABLE 2

BYD->BDO byproducts, comparative Ce—Ni

| feed pH | BuOH(%) | acetal(%) |
|---|---|---|
| 4.3 | 0.55 | 0.40 |
| 7.0 | | |
| 7.5 | | |
| 8.0 | 0.25 | 0.65 |
| 8.5 | 0.21 | 0.58 |

The principle and the embodiment of the disclosures are set forth in the specification. The description of the embodiments of the present disclosure is only used to help understand the method of the present disclosure and the core idea thereof. Meanwhile, for a person of ordinary skill in the art, the disclosure relates to the scope of the disclosure, and the technical scheme is not limited to the specific combination of the technical features, and also should covered other technical schemes which are formed by combining the technical features or the equivalent features of the technical features without departing from the inventive concept. For example, technical scheme may be obtained by replacing the features described above as disclosed in this disclosure (but not limited to) with similar features.

The invention claimed is:

1. A process of preparing a catalyst, the process comprising:

melting and mixing copper, nickel, and aluminum to form an alloy precursor, wherein nickel is present in an amount ranging from 30% to 60% by weight of the alloy precursor, and aluminum is present in an amount ranging from 40% to 65% by weight of the alloy precursor.

2. The process of claim 1, wherein Ni is present in an amount ranging from about 40% to about 49% by weight of the alloy precursor, aluminum is present in an amount ranging from about 50% to about 60% by weight of the alloy precursor, and copper is present in an amount ranging from about 1.0% to about 10.0% by weight of the alloy precursor.

3. The process of claim 2, further comprising:

contacting the alloy precursor with an alkali aqueous solution to produce the catalyst, wherein the catalyst comprises copper in an amount ranging from about 1.0% to 12.0% by weight of the catalyst.

4. The process of claim 2, wherein the catalyst is a skeletal metal catalyst.

* * * * *